(12) United States Patent
Franse et al.

(10) Patent No.: US 6,602,696 B1
(45) Date of Patent: Aug. 5, 2003

(54) ASPERGILLUS TUBIGENSIS POLYGALACTURONASE

(75) Inventors: Maartje Maria Franse, Den Haag (NL); Catherine Marie Therese Grassin, Seclin (FR); Margareta Adriana Herweijer, Den Haag (NL); Petrus Johannes Albertus Meeuwsen, Arnhem (NL); Albert Johannes Joseph Van Ooijen, Voorburg (NL); Alphons Gerard Joseph Voragen, Wageningen (NL)

(73) Assignee: DSM N. V. (NL)

( * ) Notice: Subject to any disclaimer, the term of this patent is extended or adjusted under 35 U.S.C. 154(b) by 0 days.

(21) Appl. No.: 09/787,583

(22) PCT Filed: Sep. 20, 1999

(86) PCT No.: PCT/EP99/07786

§ 371 (c)(1),
(2), (4) Date: Jun. 11, 2001

(87) PCT Pub. No.: WO00/17367

PCT Pub. Date: Mar. 30, 2000

(30) Foreign Application Priority Data

Sep. 18, 1998 (EP) ............................................ 98203171
Feb. 17, 1999 (EP) ............................................ 99200481

(51) Int. Cl.[7] ........................ C07H 21/04; C12N 15/09; C12N 9/00; C12N 1/20; C12N 15/00; C12N 9/24; C12N 9/26

(52) U.S. Cl. ...................... 435/201; 435/69.2; 435/183; 435/200; 435/252.3; 435/320.1; 536/23.2; 536/23.7; 536/23.74

(58) Field of Search ................................ 435/69.2, 183, 435/200, 201, 252.3, 320.1; 536/23.2, 23.7, 23.74; 426/56, 549; 510/114, 392, 515

(56) References Cited

FOREIGN PATENT DOCUMENTS

| EP | 0 388 593 | 9/1990 |
|---|---|---|
| EP | 0 421 919 | 4/1991 |
| WO | WO 94/14952 | 7/1994 |
| WO | WO 94/14966 | 7/1994 |

OTHER PUBLICATIONS

Bussink, H. et al. (1992) *Eur J Biochem* 208:83–90.
Parenicova, L. et al. (2000) *Biochem J* 345:637–644.
Cary et al., Gene (1995) 153(1):129–133.
He et al., J. Bacteriol. (1990) 172:4988.
Heldt–Hansen et al., in Pectins and Pectinases, Visser and Voragen (Eds.) (1996) Elsevier Science B.V.
Kitamoto et al., Fems. Microbiology Letters (1993) 3:37–42.
Pilnik et al., in The Biochemistry of Fruits and Their Products (1970) 1:53.
Whitehead et al., Applied and Environmental Microbiology (1995) 61:3316–3322.
Whitehead et al. SwissProt Accession No. P41749, 1995.*
Cary et al. SwissProt Accession No. P49575, Feb. 1996.*
Kitamoto et al. Swiss prot accession No. P35335, Jun. 1994.*

* cited by examiner

*Primary Examiner*—Rebecca E. Prouty
*Assistant Examiner*—Manjunath N. Rao
(74) *Attorney, Agent, or Firm*—Morrison & Foerster LLP

(57) ABSTRACT

The present invention relates to a DNA sequence obtainable from *Aspergillus tubigensis* which encodes a polygalacturonase. It also relates to vectors comprising the DNA sequence and to host cells transformed with such vectors. The invention further relates to the expression of the polygalacturonase and its use.

17 Claims, 4 Drawing Sheets

ASPERGILLUS TUBIGENSIS POLYGALACTURONASE

FIELD OF THE INVENTION

The present invention relates to pectin degrading enzymes, in particular to enzymes with polygalacturonase activity. More particularly, it relates to fungal enzymes with polygalacturonase activity, to polynucleotides encoding these enzymes and to the use of these enzymes in the food and feed industry.

BACKGROUND OF THE INVENTION

Pectins are major constituents of the cell walls of edible parts of fruits and vegetables. The middle lamella which are situated between the cell walls are mainly built up from protopectin, the insoluble form of pectin. Due to their colloid nature, pectins have an important function in the water regulation of plants.

Pectins are composed of a polygalacturonic acid backbone in which 1,4-linked alpha-D-galacturonan chains (smooth regions) are interrupted at intervals by the insertion of 1,2-linked alpha-rhamnopyranosyl residues (hairy regions) (Pilnik et al. (1970) In: The Biochemistry of fruits and their products, 1, 53). A varying proportion of the carboxyl groups of the polymer may be esterified with methyl groups.

Pectin degrading enzymes are important tools in the food industry, especially in the fruit and vegetable (processing) industry. *Aspergillus niger* and other fungi produce a whole range of enzymes which can advantageously be used in the degradation of the pectin polymer. Examples of such enzymes are pectin (methyl)esterase, which can remove the methyl group from the pectin, while leaving the pectin backbone intact; pectin lyase and polygalacturonases, which disintegrate the pectin backbone.

In the food industry there is sometimes a need for the individual enzyme (e.g.pectin esterase for gellification) and sometimes a need for the combined action of the different enzymes (e.g. pectin esterase plus polygalacturonase for liquefaction of plant material). Heldt-Hansen et al. (In: Pectins and pectinases, J. Visser and A. J. G. Voragen, (editors) 1996, Elsevier Science B.V.), for instance, describe how purees may be obtained by either a combination of polygalacturonase and pectin lyase, or a combination of polygalacturonase I, rhamnogalacturonase B and rhamnogalacturonase A, or a combination of pectin lyase, rhamnogalacturonase B and rhamnogalacturonase A.

These pectinases may be isolated from various microorganisms, but it is often not possible to obtain the desired enzymes in desired ratios. On the other hand, the availability of cloned pectinases allows for the preparation of tailor-made enzyme mixtures.

One of the pectinases which has been cloned is the group of polygalacturonases, which disintegrate the pectin backbone of de-esterified pectin by depolymerisation.

He et al. ( J. Bacteriol. 172, 4988, (1990)) describe the cloning of an exo-polygalacturonase from *Erwinia chrysanthemi*.

WO 94/14952 describes three enzymes with endopolygalacturonase activity which are obtainable from *Aspergillus aculeatus*.

EP 0 421 919 describes an enzyme with polygalacturonase activity which is obtainable from *Aspergillus niger*.

EP 0 388 593 describes the expression of an endopolygalacturonase from *Aspergillus niger*.

There is still a need for pectin-degrading enzymes with new properties, which are a useful addition to the existing range of pectinases.

DESCRIPTION OF THE INVENTION

Figure 1:
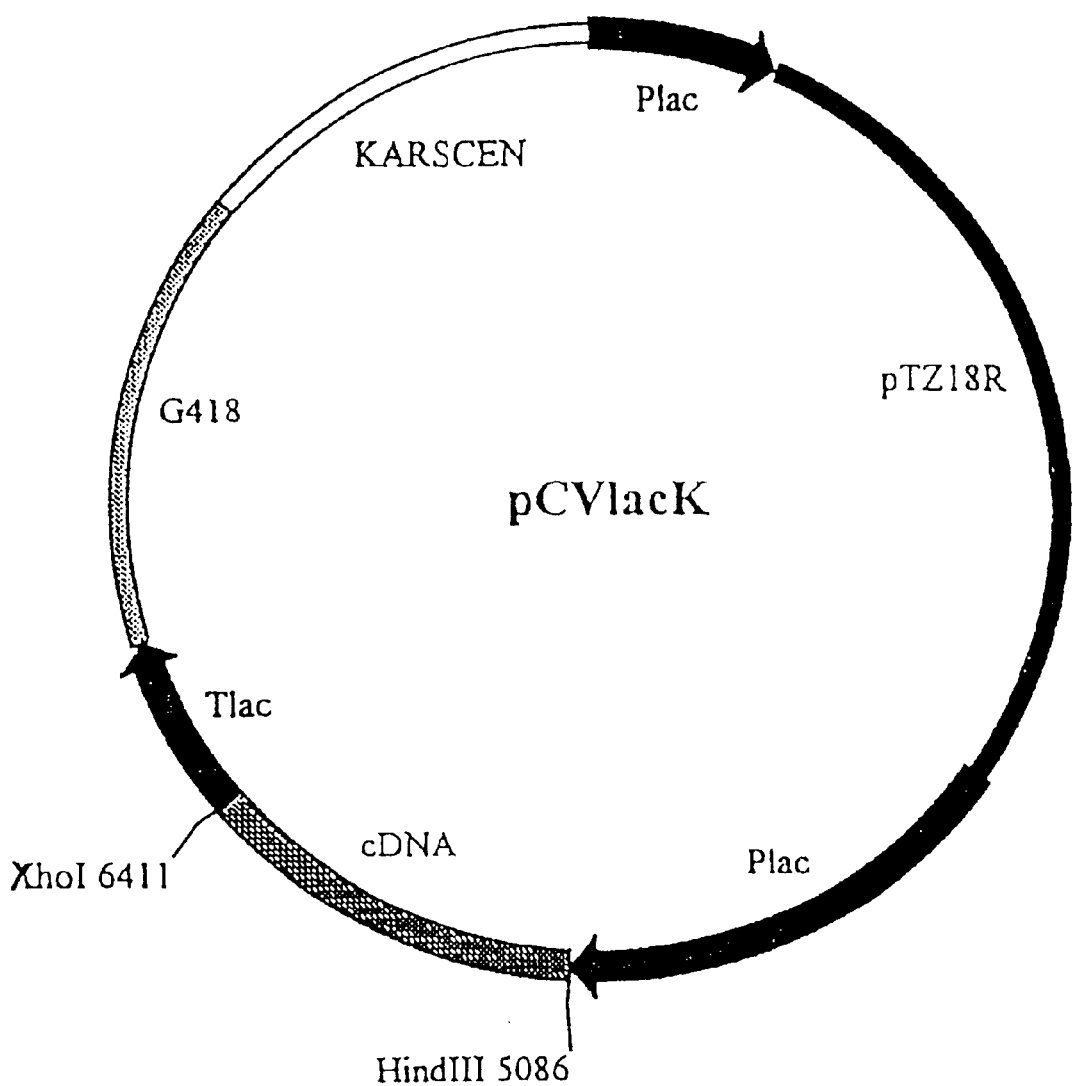
FIG. 1 shows the map of vector pCVlacK.

The present invention discloses a polynucleotide molecule which comprises a sequence which encodes an enzyme with polygalacturonase activity. The sequence which is comprised in the polynucleotide molecule is shown in SEQ ID No. 1 and is quite different from known polygalacturonase encoding sequences.

The invention also relates to the polypeptide encoded by the polynucleotide sequence of the invention. This polypeptide with polygalacturonase activity has a high temperature optimum. Therefore, one of the advantages of the present inventionis that it provides enzymes which are extremely suitable to be used in high temperature applications.

It also has a broad pH optimum, which makes it extremely suitable to be used not only at high pH but also at low pH.

The present invention also relates to the use of the polypeptide in industrial applications in the feed and food industry.

The disclosure of the polynucleotide sequence that encodes this enzyme with polygalacturonase activity makes it possible to design tailor-made combinations of this enzyme and other compounds, e.g., other enzymes, for specific applications.

Polynucleotides

The invention encompasses polynucleotide molecules which comprise a polynucleotide sequence as shown in SEQ ID No. 1 and which encode an enzyme with polygalacturonase activity. The polygalacturonase activity is preferably endopolygalacturonase activity (EC 3 2.1.15).

The invention also encompasses polynucleotide molecules which encode allelic variants of the enzyme with polygalacturonase activity.

The invention further encompasses polynucleotide molecules which comprise a polynucleotide sequence which encodes a polypeptide with the sequence of SEQ ID No.2.

The invention also relates to polynucleotide molecules which encode polypeptides with polygalacturonase activity and which are homologues to SEQ ID No.1. The homologues may be at least more than 70%, preferably more than 80%, more preferably more than 90% or 95% identical, if 'DNAsis for Windows Ver. 2.5' (Hitachi Software Engineering) is used for the comparison of DNA sequences. The following parameters were set for the multiple alignments: gap penalty (5) and floating gap penalty (10).

Polynucleotides of the invention, which are typically provided in isolated and/or purified form, may comprise DNA or RNA. They may also be polynucleotides which include within them synthetic or modified nucleotides. For the purposes of the present invention, it is to be understood that the polynucleotides described herein may be modified by any method available in the art.

Polynucleotides, such as, a DNA polynucleotide and primers according to the invention may be produced recombinantly, synthetically, or by any means available to those skilled in the art. Primers according to the invention may be used to identify polynucleotides of the invention using routine techniques.

The polynucleotide of the invention may be operably linked to expression regulatory sequences. Expression regulatory sequences enable the expression of a polypeptide of the invention. They comprise at least a promoter region and a structural gene and optionally a signal sequence and a transcription termination region. They may also comprise further regulatory sequences, such a transcriptional enhancer.

The polynucleotides of the invention may be part of both cloning and expression vectors. These vectors may carry one or more selection markers.

Alternatively the polynucleotide of the invention may be integrated in the genome.

Polypeptides

The invention encompasses polypeptides which comprise an amino acid sequence as shown in SEQ ID No. 2 and typically have polygalacturonase activity.

The invention also encompasses polypeptides which are allelic variants of polypeptides with an amino acid sequence as shown in SEQ ID No. 2.

The invention further encompasses polypeptides with polygalacturonase activity which have a sequence which is homologous to SEQ ID No.2.

The homologous polypeptide may be more than 75% identical to SEQ ID No. 2, preferably 80% or 90%, and more preferably at least 95% identical thereto, if 'DNAsis for Windows Ver. 2.5' (Hitachi Software Engineering) is used for the comparison of amino acid sequences. The following parameters were set for the multiple alignments: gap penalty (5) and floating gap penalty (10).

The polypeptide of the invention may be derived from a fungus, such as a filamentous fungus. Preferably the (filamentous) fungus is of the species *Aspergillus oryzae, Aspergillus sojae, Aspergillus nidulans*, species from the *Aspergillus niger* Group (as defined by Raper and Fennell, The Genus Aspergillus, The Williams & Wilkins Company, Baltimore, pp 293–344, 1965), specifically including but not limited to *Aspergillus niger, Aspergillus awamori, Aspergillus tubigensis, Aspergillus aculeatus, Aspergillus foetidus, Aspergillus japonicus* and *Aspergillus ficuum*.

In the context of the invention the term "derived from" includes both polypeptides which naturally occur in or are produced by these fungi and polypeptides which are not naturally occurring. The term also includes fragments of such polypeptides.

The polypeptide of the invention or fragments thereof may be used to identify polypeptides with polygalacturonase activity in other species or organisms. For example, they may be used for the production of antibodies. Methods for the production of antibodies are well known to the skilled person.

The sequence of the polypeptide of SEQ ID No. 2 and of homologues and allelic variants can be modified to provide polypeptides of the invention. These modified polypeptides may retain polygalacturonase activity, but they do not necessarily.

Recombinant Production

For the recombinant production of the polypeptide of the invention a DNA sequence of the invention is used for gene amplification and/or exchange of expression signals, such as promoters, secretion signal sequences, in order to allow economic production of the polypeptide of the invention in a suitable homologous or heterologous host cell. A homologous host cell is herein defined as a host cell which is the same, or of the same species or which is a variant within the same species as the species from which the DNA sequence is derived. Suitable host cells are preferably microorganisms like bacteria, or more preferably fungi such as yeasts or filamentous fungi. A preferred yeast host cell for the expression of a DNA sequence encoding the polypeptide of the invention is selected from the group consisting of the genera Saccharomyces, Kluyveromyces, Hansenula, Pichia, Yarrowia, and Schizosaccharomyces. More preferably a yeast host cell is selected from the group consisting of the species *Saccharomyces cerevisiae, Kluyveromyces lactis* (also known as *Kluyveromyces marxianus var. lactis*), *Hansenula polymorpha, Picihia pastoris, Yarrowia lipolytica*, and *Schizosaccharomyces pombe*.

Most preferred for the expression of a DNA sequence encoding the polypeptide of the invention are, however, filamentous fungal host cells. Preferred filamentous fungal host cells are selected from the group consisting of the genera Aspergillus, Trichoderma, Fusarium, Penicillium, Acremonium, Neurospora, Thermoascus, Myceliophtora, Sporotrichum, Thielavia, and Talaromyces. More preferably a filamentous fungal host cell is selected from the group consisting of the species *Aspergillus oryzae, Aspergillus sojae, Aspergillus nidulans*, species from the *Aspergillus niger* Group as defined by Raper and Fennell (1965, In: The Genus Aspergillus, The Williams & Wilkins Company, Baltimore, pp 293–344), specifically including but not limited to *Aspergillus niger, Aspergillus awamori, Aspergillus tubigensis, Aspergillus aculeatus, Aspergillus foetidus, Aspergillus japonicus* and *Aspergillus ficuum*, and further consisting of the species *Trichoderma reesei, Fusarium graminearum, Penicillium chrysogenum, Acremonium alabamense, Neurospora crassa, Myceliophtora thermophilum, Sporotrichum cellulophilum*, and *Thielavia terrestris*.

The expression construct can be used for transformation of the host as part of a vector carrying a selectable marker, or the expression construct is co-transformed as a separate molecule together with the vector carrying a selectable marker. Suitable selectable markers which can be used for selection of the transformed host cells are well known to the skilled person (Goosen et al., 1992, In: Handbook of Applied Mycology" 4: "Fungal Biotechnology", and Romanos et al., 1992, Yeast 8: 423).

Preferred markers include but are not limited to e.g. versatile marker genes that can be used for transformation of most filamentous fungi and yeasts such as acetamidase genes or cDNAs (the amdS genes or cDNAs from *A.nidulans, A.oryzae*, or *A.niger*), or genes providing resistance to antibiotics like G418 or hygromycin or phleomycin.

Alternatively, more specific selection markers can be used such as auxotrophic markers which require corresponding mutant host strains: e.g. URA3 (from *S.cerevisiae* or analogous genes from other yeasts), pyrG (from *A.nidulans* or *A.niger*) or argB (from *A.nidulans* or *A.niger*). In a more preferred embodiment, the selection marker is deleted from the transformed host cell after introduction of the expression construct in accordance with the methods described in EP-A-0 635 574, so as to obtain transformed host cells capable of producing the polypeptide which are free of selection marker genes.

For most filamentous fungi and yeast, the expression construct is preferably integrated in the genome of the host cell in order to obtain stable transformants. However, for certain yeasts also suitable episomal vector systems are available into which the expression construct can be incorporated for stable and high level expression, examples thereof include vectors derived from the 2μ and pKD1 plasmids of *Saccharomyces and Kluyveromyces*, respectively. In case the expression constructs are integrated in the host cells genome, the constructs are either integrated at random loci in the genome, or at predetermined target loci using homologous recombination, in which case the target loci preferably comprise a highly expressed gene. A highly expressed gene is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l. A number of examples of suitable highly expressed genes is provided herein below.

An expression construct for a given host cell will usually contain the following elements operably linked to each other in a consecutive order from the 5'-end to 3'-end relative to the coding strand of the sequence encoding the polypeptide of the invention: (1) a promoter sequence capable of directing transcription of the DNA sequence encoding the polypeptide in the given host cell, (2) optionally, a signal sequence capable of directing secretion of the polypeptide from the given host cell into the culture medium, (3) the DNA sequence encoding a mature and preferably active form of the polypeptide, and preferably also (4) a transcription termination region (terminator) capable of terminating transcription downstream of the DNA sequence encoding the polypeptide.

A variety of promoters capable of directing transcription in the host cells of the invention is available to the skilled person (Goosen et al., 1992, In: Handbook of Applied Mycology" 4: "Fungal Biotechnology", and Romanos et al., 1992, Yeast 8: 423).

Preferably the promoter sequence is derived from a highly expressed gene as previously defined. Examples of preferred highly expressed genes from which promoters are preferably derived and/or which are comprised in preferred predetermined target loci for integration of expression constructs, include but are not limited to genes encoding glycolytic enzymes such as triose-phosphate isomerases (TPI), glyceraldehyde-phosphate dehydrogenases (GAPDH), phosphoglycerate kinases (PGK), pyruvate kinases (PYK), alcohol dehydrogenases (ADH), as well as genes encoding amylases, glucoamylases, xylanases, cellobiohydrolases, β-galactosidases, alcohol (methanol) oxidases, elongation factors and ribosomal proteins. Specific examples of suitable highly expressed genes include e.g. the LAC4 gene from Kluyveromyces sp., the methanol oxidase genes (AOX and MOX) from Hansenula and Pichia, respectively, the glucoamylase (glaA) genes from *A.niger* and *A.awamori*, the *A.oryzae* TAKA-amylase gene, the *A.nidulans* gpdA gene and the *T.reesei* cellobiohydrolase genes.

Preferably the polypeptide is produced as a secreted protein in which case the polynucleotide sequence encoding a mature form of the polypeptide in the expression construct is operably linked to a polynucleotide sequence encoding a signal sequence. Preferably the signal sequence is native (homologous) to the DNA sequence encoding the polypeptide. Alternatively the signal sequence is foreign (heterologous) to the DNA sequence encoding the polypeptide, in which case the signal sequence is preferably endogenous to the host cell in which the DNA sequence is expressed. Examples of suitable signal sequences for yeast host cells are the signal sequences derived from yeast alpha-factor genes. Similarly, a suitable signal sequence for filamentous fungal host cells is e.g. a signal sequence derived from a filamentous fungal (gluco)amylase gene, e.g. the *A.niger* glaA gene.

Downstream of the DNA sequence encoding the polypeptide, the expression construct preferably contains a 3' untranslated region containing one or more transcription termination sites, also referred to as a terminator. The origin of the terminator is less critical. The terminator can e.g. be native to the DNA sequence encoding the polypeptide. However, preferably a yeast terminator is used in yeast host cells and a filamentous fungal terminator is used in filamentous fungal host cells. More preferably, the terminator is endogenous to the host cell in which the DNA sequence encoding the enzyme with polygalacturonase activity is expressed.

The recombinant host cells according to the invention may be cultured using procedures known in the art. For each combination of a promoter and a host cell, culture condition are available which are conducive to the expression the DNA sequence encoding the polypeptide. After reaching the desired cell density or titre of the polypeptide the culture may be stopped and the polypeptide may be recovered using known procedures.

Compositions

The invention also provides a composition comprising a polygalacturonase of the invention. Optionally, one or more other enzymes may be present. It also provides a composition comprising a recombinant host cell of the invention.

The compositions of the invention may be in a form suitable for packaging and/or storage. In a composition which comprises the polypeptide of the invention the composition is generally of a form in which the polygalacturonase activity of the polypeptide is substantially retained. The polypeptide in the composition may be attached to or mixed with a carrier, for example the polypeptide may be immobilized, such as on a solid carrier.

In a composition which comprises host cells of the invention the composition will generally be of a form which allows some or all of the host cells to remain viable. The composition may additionally comprise nutrients for the host cell, which are provided to the host cell when it is cultured.

The composition may be in a form suitable for the process in which it will be used. The composition may be formulated in any convenient way, including as a paste, liquid, emulsion, powder, flakes, granulate, pellet or other extrudate.

The composition may comprise additional substances which aid the pectin degrading activity of the composition. Thus the composition may additionally comprise other enzymes. These other enzymes may be recombinant enzymes, or may have been obtained from an organism in which they occur naturally. The enzymes may have been substantially purified before addition to the composition of the invention, or they may be left substantially unpurified before being added to the composition of the invention.

Non-limiting examples of such other enzymes are pectin degrading and/or modifying enzymes, (hemi-)cellulose degrading and/or modifying enzymes, proteases, starch degrading and/or modifying enzymes, lipases, phosphatases, phytases.

The composition may comprise organisms (e.g. bacteria, fungae or yeast) which produce the above mentioned enzymes or other valuable compounds which are of use in the application.

The composition may additionally comprise (particularly when being formulated for use in animal feed) one or more ionophores, oxidising agents, surfactants, rumen protected amino acids, enzyme enhancers or enzymes which may be produced naturally in the gastro intestinal tract of the animals to be fed.

A composition comprising a polypeptide of the invention is succesfully used as macerating enzyme, e.g. for the preparation of fruit and vegetable purees. These purees have a more smooth consistency than purees made mechanically or by using known polygalacturonases. If a composition of the invention is used for maceration it should be free of pectin esterase activity for best results.

Compositions of the invention may be used in the detergent industry, e.g. for the removal of food stains.

A composition of the invention may also be used to prepare pectins with modified characteristics. Alternatively, it may be used as a prebioticum or to prepare a prebioticum.

The invention provides the use of a polypeptide, host cell or composition of the invention to degrade pectin. Thus the invention provides a method of degrading pectin comprising contacting a polypeptide, host cell or composition of the invention with the pectin to be degraded.

In the method all or part of the pectin may be degraded, for example from 0 to 20%, 20 to 40%, 40 to 50%, 50 to 70% or 70 to 100% by weight may be degraded.

The pectin which is degraded in the method of the invention may be derived from a plant or may have been synthetically produced by man.

The method of degrading pectin of the invention may be part of a method for producing or processing food or beverages or animal feed.

Since the polygalacturonases of the invention are more thermostable than known polygalacturonases the polygalacturonases of the invention can be used in a much wider range of application conditions. Since they have broader pH optimum than known polygalacturonases, polygalacturonases of the invention can also be used at low pH, which is very advantageous for fruit juice applications.

Polygalacturonases in combination with other pure or crude pectinase containing enzyme mixtures may also be added to animal feed compositions which are rich in pectin. When added to feeds (including silage) for ruminants or monogastric animals (eg. poultry or swine) which feeds contain cereals such as barley, wheat, maize, rye or oats or cereal by-products such as wheat bran or maize bran, or other plant materials such as soy beans and other legumes, the enzyme(s) significantly improve the break-down of plant cell walls which leads to better utilization of the plant nutrients by the animal. As a consequence, growth rate and/or feed conversion are improved.

The polygalacturonases of the invention may also be used for the maceration of plant cell wall material in fruits and vegetables, e.g. in the food industry.

The following examples illustrate the invention.

EXAMPLES

Example 1

Construction of the *Aspergillus tubigensis* cDNA Expression Library

Example 1.1

Construction of an Expression Vector

Starting vector pGBHSA20 (CBS 997.96) contains the promoter and terminator sequence of the lactase gene (lac4) of *K. lactis*, a G418 selection marker and the *E. coli* plasmid pTZ18r for propagation in this host. A *K. lactis* KARS-CEN cassette (a gift from Dr. A. A. Winkler, Dept. of Cell Biology and Genetics, Leiden University, The Netherlands; Winkler, A. A. 1998, PhD Thesis, University of Leiden, the Netherlands) was cloned in a unique SmaI site of this vector. The resulting vector was named pCVlacK (FIG. 1). The unique HindIII and XhoI sites flanking the lac4 promoter and terminator, respectively, can be used as cloning sites for cDNA synthesized from *Aspergillus tubigensis* poly(A) RNA.

Example 1.2

Isolation of Poly(A) RNA and cDNA Synthesis

*Aspergillus tubigensis* conidia were inoculated in triplo at a density of $10^6$ spores/ml in 300 ml of medium containing (per liter): 6 g $NaNO_3$, 0.5 g KCl, 1.5 g $KH_2PO_4$, 0.5 g $MgSO_4$, pH 6.5, 1 ml 1000× Timberlake spore elements (per ml, 50 mg EDTA, 22 mg $FeSO_4.7H_2O$, 5 mg $MnCl_2.2H_2O$, 22 mg $ZnSO_4.7H_2O$, 1.6 mg $CuSO_4.5H_2O$, 1.7 mg $CoCl_2.6H_2O$, 1.5 mg $Na_2MoO_4.2H_2O$, 11 mg $H_3BO_3$, adjusted to pH 6.5) and 10 ml 100× Timberlake vitamins (per ml, 0.2 mg thiamine-HCl, 0.2 mg riboflavin 0.2 mg nicotinamide, 1 mg pyridoxine-HCl, 0.02 mg panthothenic acid, 0.4 μm biotin, adjusted to pH 5 to 6), 1 g yeast extract, 5 g Soyoptim (defatted, toasted soy bean meal from Societe Industrielle Oleagineux, France). The cultures were incubated in a rotary shaker at 28° C., 150 rpm. The mycelium of one culture was harvested at 10 hours after inoculation, mycelium of the other two cultures was harvested at, respectively, 16 and 24 hours after inoculation. From 1 g rinsed and squeezed mycelium total RNA was isolated by the RNAzol method (Cinna/Biotecx). Poly(A) RNA was isolated using Qiagen oligotex columns (Westburg). Equal amounts of poly(A) RNA of time-points 10, 16 and 24 hours, were pooled. cDNA was synthesized using the ZAP-cDNA synthesis kit (Stratagene) with the following modifications: the first-strand synthesis was done with Superscript II reverse transcriptase (GibcoBRL). To 7.5 μg poly(A) RNA, 2 μl linker-primer and RNAse free water was added to a final volume of 28.5 μl. This mixture was incubated for 10 minutes at 70° C. and chilled on ice. The following components were added. 10 μl 5× first strand buffer, 5 μl 0.1 M DTT, 3 μl first-strand methyl nucleotide mixture and 1 μl RNAse block. This was incubated for 10 minutes at 25° C., followed by 2 minutes at 42° C. Subsequently, 2.5 μl Superscript II RT (200 U/μl) was added, mixed and incubated for 50 minutes at 42° C. A second modification of the protocol was ligation of a HindIII adaptor instead of the EcoRI adaptor.

The cDNA pool was size separated using a Sephacryl S-500 column. The first fraction eluted from the column did not contain any cDNA, the second and third fractions contained the largest sized cDNA. Subsequent fractions were supposed to contain relatively higher amounts of non-full length cDNA and were of no use for construction of the library. The cDNA of fractions 2 and 3 was ligated in the HindIII and XhoI sites of expression vector pCVlacK (see FIG. 1) using the Clontech Ligation Express™ kit. Each ligation mixture was transformed in two batches to electrocompetent *E. coli* XL-Blue MRF' cells. The four transformation suspensions were plated onto 32 agar plates (LB+50 microg/ml ampicillin). After 16 hours of incubation at 37° C., 7366 transformants were obtained. Bacteria were collected by pouring 2.5 ml LB medium onto a plate and scraping off the cells; 0.5 ml of cell suspension was added to glycerol and stored at −80° C., the remaining 2 ml was used for DNA isolation (Qiagen Spin miniprep kit). In case of a low number of transformants per plate, the 2.5 ml was transferred to a second, third or fourth plate. This yielded 22 pools of about 325 individual transformants. Equal amounts of DNA of each pool were combined for use in *K. lactis* transformation.

Example 1.3

Transformation of the Expression Library into *K. lactis*

An overnight culture of *K. lactis* strain CBS 2359 grown in YPD (10 g/l yeast extract, 20 g/l Bacto-peptone, 20 g/l glucose) at 30° C. was diluted 3 000-, 600-, 300-, and 100-fold in 1 50 ml of fresh YPD and incubated for 6 hours at 30° C., 160 rpm in a rotary shaker. The culture with an optical density of 0.7–1.0 was used to prepare electrocompetent cells according to K. N. Faber et al. (1994) Current genetics 25: 305–310.

Electrocompetent cells were transformed with 1 µg pooled DNA of the *E. coli* library. Electroporation was performed using a Biorad Genepulser with settings at 1.4 kV, 200 Ohm and 25 µF. Transformants were selected on YPD plates (YPD with 15 g/l Bacto-agar) containing 50 microgram/ml of the antibiotic G418.

Aliquots of 50, 100 and 200 µl were pipetted onto the plates. About 10 000 transformants were obtained.

Example 2

Screening of the Library

Example 2.1

Growth of the Transformants

From the about 10 000 *K. lactis* transformants produced as described in Example 1.3, 5 000 individual colonies were picked and transferred to separate wells of multiwell plates, using a colony-picking robot (FLEXYS colony-picker from PBA Technology).

The transformants in the multiwell plates were grown for 48 hours at 30° C. in YPD medium (10 g/l yeast extract, 20 g/l Bacto-peptone, 20 g/l glucose) containing 50 µg/ml of the antibiotic G418 and the 50 plates were stored as 10% glycerol stocks.

These transformants were used to inoculate, with the replica-plating tool of the FLEXYS colony-picker (PBA technology), YPG (10 g/l yeast extract, 20 g/l Bacto-peptone, 10 g/l galactose and 15 g/l Bacto-agar) plates having the same format as the multi well plates.

The *K. lactis* transformants were grown for 48 hours at 30° C. in a stove.

Example 2.2

Ruthenium Red Plate Assay for Polygalacturonase Activity

Colonies were grown on solid YPG (10 g/l yeast extract, 20 g/l Bacto-peptone, 10 g/l galactose with 15 g/l Bacto-agar). An overlay with polygalacturonic acid (1% agarose, 0.2% polygalacturonic acid (ICN, cat. 102711), 50 mM acetate buffer pH 5) was poured over the colonies and the plates were incubated for 6 hours at 30° C. to let the secreted enzymes degrade the substrate. After incubation, a 0.05% ruthenium red (Serva) solution, was poured on the plates folowed by an incubation at 30° C. for 30 minutes. The ruthenium red solution was carefully washed from the plates with water. Ruthenium red adheres to polygalacturonic acid, leaving colonies which have secreted an enzyme degrading this substrate with an uncoloured halo within a red background. Two colonies out of the 5 000 were surrounded by such a halo. References of these colonies are AB03231 and AB04608.

Example 3

Characterization of Polygalacturonase Encoding cDNA

*K. lactis* transformants AB03231 and AB04608, exhibiting polygalacturonase activity, were used to isolate the pCVlacK expression plasmids by the glass beads method (Current Protocols in Molecular Biology by John Wiley & Sons, Inc. (1997) 13.11.1). After transformation and propagation of the plasmids in *E. coli*, the cDNA inserts were excised from pCVlacK plasmids with a HindIII/XhoI digestion. The digestions release a 1.3 kilobasepair (kb) fragment in both cases. The DNA sequence of the cDNA inserts from clone AB03231 and AB04608 was determined using a 5'-specific primers to the lac4 regulating sequence. Analysis of the obtained sequences showed that the plasmid inserts of these two transformants were identical. The full length DNA sequence of the cDNA insert from clone AB03231 was determined on both strands using 5'- and 3'-specific primers to the lac4 regulating sequences and primers based on the cDNA sequence. The DNA sequence of the cDNA insert is presented in SEQ ID No 1, together with the deduced amino acid sequence. Upstream of the ATG translation startcodon, 96 basepairs (bp) of 5'-untranslated sequence are present. Downstream the TAA stopcodon, 108 bp non-translated sequence followed by the poly-A tail are found. The open reading frame of 1086 bp encodes a protein of 362 amino acids, presented in SEQ ID No 2.

Comparison of the amino acid sequence to protein databases showed homology to polygalacturonase sequences of prokaryotes, fungi and plants. The identity on amino acid sequence is 76% with pecA from *A. parasiticus* (Cary et al. (1995), Gene 153 (1), 129–133), 75% with a pecA from *A. flavus* (Whitehead et al. (1995), Appl. Environ. Microbiol. 61 (9), 3316–3322) and 75% with a polygalacturonase from *A. oyzae* (Kitamoto et al. (1993) FEMS Microbiol. Lett. 111 (1), 3741).

Based on a comparison with the derived amino acid sequences from the *A. niger* genes pgal (Bussink et al. (1991) Curr. Genet. 20 (4), 301–307), pgaII (Bussink et al. (1990) FEBS Lett. 273 (1–2), 127–130), pgaE (Parenicova et al. (1998) Eur. J. Biochem. 251, 72–80) and pgaC (Bussink et al. (1992) Appl. Microbiol. Biotechnol. 37, 324–329), it is assumed that the protein encoded by the AB03231 sequence is synthesized as a preproprotein with a 26 amino acid extension. The putative prepro sequence is cleaved after Lys25, Arg26 by a dibasic endopeptidase processing in analogy to the KEX2-encoded protease of *S. cerevisiae* (Calmels et al. (1991) J. Biotechnol. 17, 51–66).

Comparison of the mature polypeptides of the derived amino acid sequences of the described polygalacturonase genes from *A. niger* gives 53% homology for the pgaII, 52% for pgaI, 43% for pgaC and 42% for pgaE when compared with the mature protein encoded by AB03231.

The fact that the highest homology on amino acid level with the other four endopolygalacturonases from *A. niger* is only 53% indicates that the endopolygalacturonase encoded by the sequence AB03231 is a new member of the endopolygalacturonase gene family from *A. niger*.

Example 4

Production of the Enzyme

Example 4.1

Integration of cDNA into Genome of *K. lactis*

The pCVlacK expression plasmid of transformant AB03231 was cut by the restriction enzyme NruI to eliminate the KARS-CEN sequence. DNA was separated on a 1% agarose gel and the linearized plasmid, containing the CDNA but lacking the KARS-CEN sequence, was isolated, followed by a ligation reaction (Current Protocols in Molecular Biology by John Wiley & Sons, Inc. (1997) 3.14.1). This plasmid was propagated in *E. coli* and subsequently linearized by the restriction enzyme HpaI. Electrocompetent cells of *K. lactis* strain CBS 2359 were transformed with 1 μg of linearized plasmid as described in Example 1.3. 24 colonies were inoculated on YPG agar plates (10 g/l yeast extract, 20 g/l Bacto-peptone, 10 g/l galactose with 15 g/l Bacto-agar), followed by a ruthenium red assay for polygalacturonase activity, as described in Example 3.2. All 24 colonies showed polygalacturonase activity.

One of these clones was inoculated in YPD medium and after growth at 30° C. for 48 hours, vials were prepared with 1ml of culture to which 10% glycerol was added. These vials are stored at −80° C. and the strain will be referred to as AB03231.I.

Example 4.2

Growth of the Transformant and Production of the Enzyme

For production 1 vial was transferred into an erlenmeyer flask containing 200 ml of a medium containing: glucose 20 g/l; $NH_4H_2PO_4$ 3 g/l; $KH_2PO_4$ 0.5 g/l; $(NH_4)_2SO4$ 1 g/l; $CaCl_2$ 0.02 g/l; $MgSO_4.7H_2O$ 0.3 g/l; 1 drop of soy oil per liter as antifoam, G418 1 microgram/ml and 0.2 ml of a stock solution of trace elements containing: $H_3BO_4$ 750 mg/l; $CUSO_4.7H_2O$ 80 mg/l; KI 150 mg/l; $MnSO_4.4H_2O$ 600 mg/l; $Na_2MoO_4$ 300 mg/l; $ZnSO_4.7H_2O$ 600 mg/l; $FeCl_3.6H_2O$ 400 mg/l, and 0.2 ml of a stock solution of vitamins containing: vitamins Ca-pantothenate 1000 mg/l; thiamine 1000 mg/l; myo-inositol 1000 mg/l; ascorbic acid 1000 mg/l; pyridoxine 1000 mg/l; biotine 1 mg/l. This culture was incubated at 30° C. in a rotary incubator at 280 rpm for 5 days. Cells were harvested by centrifugation and the supernatant was concentrated by ultrafiltration.

Example 5

Biochemical Properties of the Enzyme

Example 5.1

Molecular Weight

Enzyme sample prepared according to Example 4.2 was analyzed by SDS—PAGE electrophoresis on an acrylamide gradient of 4–15%, according to a method adapted from Laemmli. Following the electrophoresis the gel was stained with Coomassie Brilliant Blue. As compared to control sample prepared from an untransformed CBS 2359 strain two additional bands at 42 and 37 kDa appear on the gel.

Example 5.2

Influences of pH and Temperature on Enzyme Activity

Enzyme sample prepared according to Example 4.2 was used to determine the influences of pH and temperature on the enzymatic activity. The properties of the enzyme are compared with the properties of endopolygalacturonase II (EndoPGII) from *Aspergillus tubigensis* (H. J. D. Bussink, H. C. M. Kester, J. Visser (1990) FEBS Lett 273, 127–130).

Endopolygalacturonase activity was determined by measuring viscosity using a Lauda viscosimeter. The variation of the 1/g (g: viscosity) in function of the reaction time allows to determine an appearing velocity which value is proportional to the enzymatic activity of the sample. One polygalacturonase unit (PG) is the enzyme quantity which induces a variation of viscosity with a velocity of which the appearing constant is 0.053 minutes$^{-1}$ in the described conditions. The activity is the number of units per gram or per mililiter of the enzyme sample.

For each assay, a standard solution of known polygalacturonase units was prepared at the beginning and at the end of the experiment.

The substrate was prepared as follows: 3.5 g of polygalacturonic acid solution (SIGMA, Sodium Salt, P 1879) were dissolved in about 80 ml of distilled water and 10 ml of acetate buffer 0.5M pH 4.70, then the pH was adjusted to 4.50 with a NaOH solution and the solution was made up to 100 ml with distilled water, then filtrated through a cotton plug.

Both references and enzyme samples were prepared by dissolving 0.3 and 0.6 endo-PG units per mililiter in 1% NaCl. Enzyme sample prepared according to Example 4.2 was used to determine the influences of pH and temperature on the enzymatic activity. The properties of the enzyme are compared with the properties of endopolygalacturonase II (EndoPGII) from *Aspergillus tubigensis* (H. J. D. Bussink, H. C. M. Kester, J. Visser (1990) FEBS Lett 273, 127–130) Measurement:

The viscosimeter was equilibrated at 45° C. before the beginning of the assay. 20 ml of the substrate were put in a tube and were equilibrated at 45° C. for 10 minutes at least. 2 ml exactly of the enzyme sample solution were added and the chronometer was started immediatly. The solution was stirred and 18 ml exactly were put into the viscosimeter tube. After 2 minutes the start button was pressed and the time T given by the chronometer when the green aperture from the marker 1 switches off was noted. The time Dt from the passage of the liquid through the two markers was printed automatically. Decrease of viscosity was measured automatically four times. For each assay, the time t of each measure was calculated: $t=T+Dt/2$ and for each Dt, the ratio $X=60/Dt$ was determined. The velocity constant K was calculated: $K=P*60$ wherein P is the slope of the graph $X=f(t)$. Activity was calculated as follows: Activity=K/(0.053*C)

Where 0.053 corresponds to the definition of the PG unit
C: the dilution factor from the sample solution For the determination of the pH optimum, the substrate solution was prepared in acetate buffers varying in pH from 3.5 to 5.5. The activity was measured according to the assay procedure described above.

For the determination of the temperature optimum, the substrate solution was prepared according to the assay procedure described above, and the activity was measured at different incubation temperatures ranging from 20 to 65° C.

Figure 2:
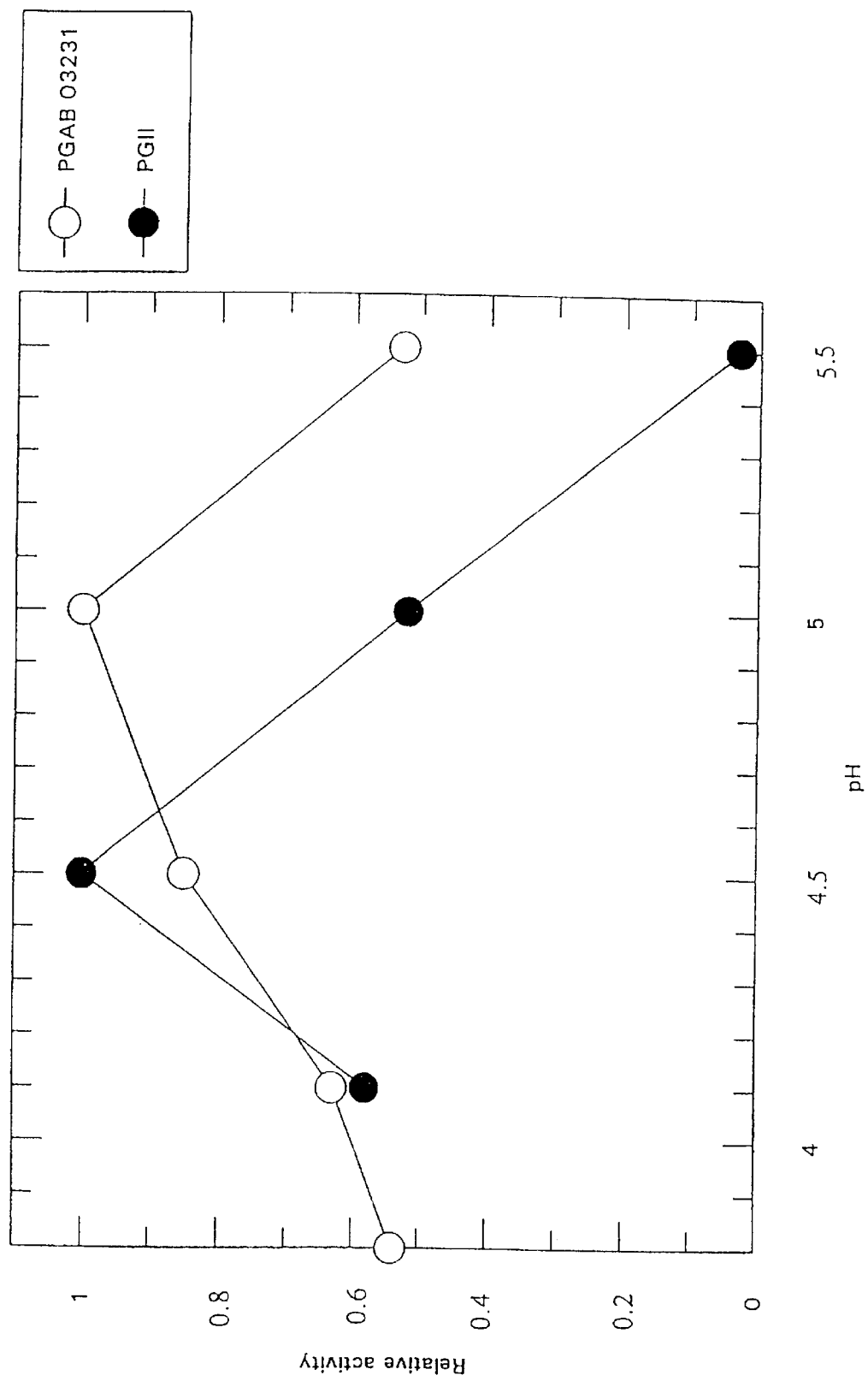
FIG. 2 shows the effect of pH on the activity of the enzyme of the invention.

FIG. 2 shows that the enzyme has an optimum activity at a pH of 5, and that it has at least 50% of its optimal activity over the whole measured range from 3.8 to 5.5. As compared with endoPGII, the endopolygalacturonase of the invention is highly active over a much broader pH range.

Figure 3:
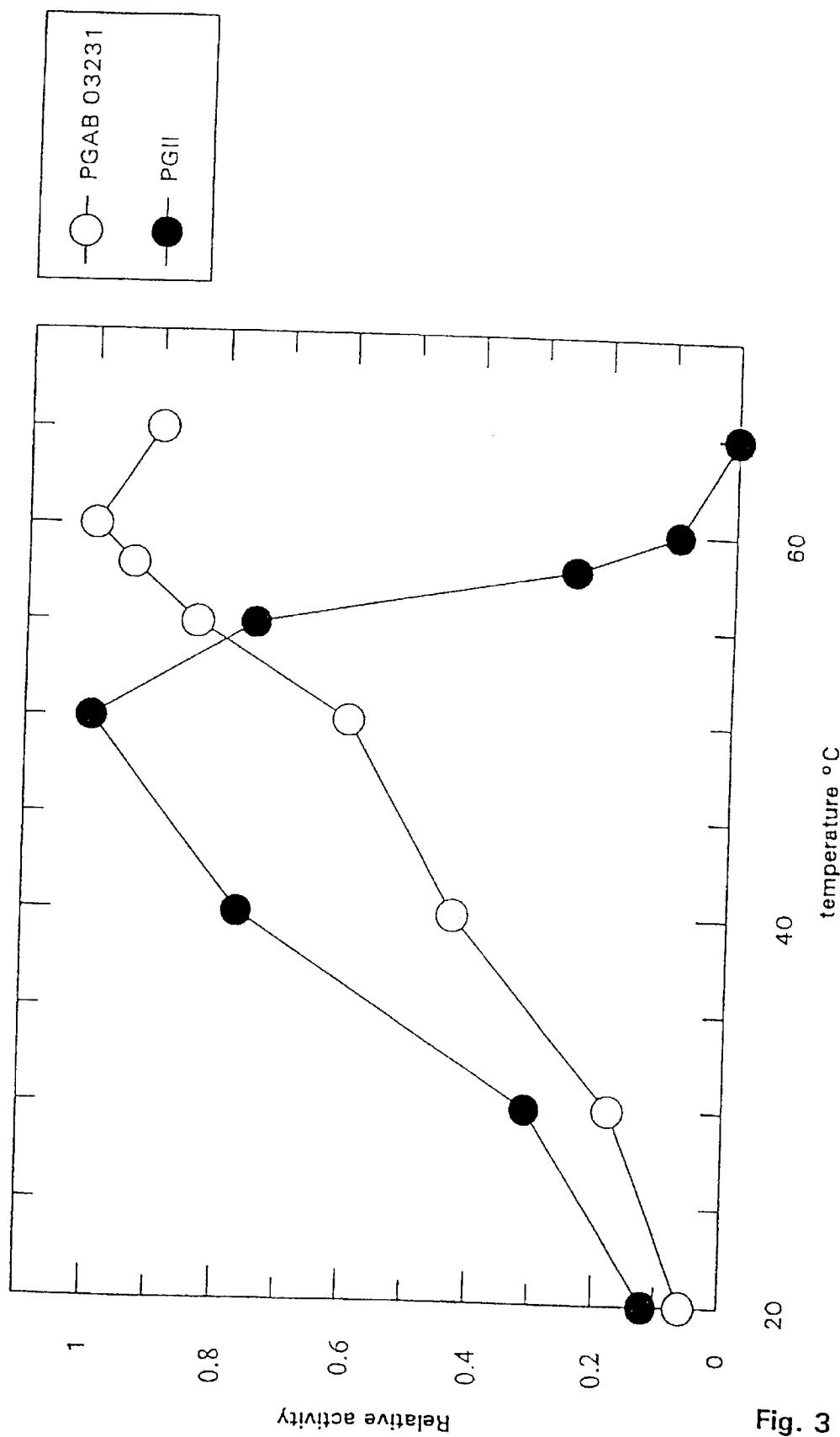
FIG. 3 shows the effect of temperature on the activity of the enzyme of the invention.

FIG. 3 shows that under the conditions of the assay the enzyme is optimally active at a temperature of 60° C. It is much more stable as compared with endoPGII. Whereas the enzyme of the invention still has 90% of its opimal activity at 65° C., endoPGII is completely inactivated at that temperature.

Example 6

Preparation of Carrot Purees

According to the invention, the effect of the enzyme was tested on a carrot purée preparation. 3 kg of carrots were peeled, cut in slices of 2 to 3 mm thick, blanched for 5 min in boiling water, and crushed in a knives mill (Retsch Mülle, type WRB90/LB4P) with three rotating knives and 2–3 mm sieve. 15 ml of a 3% ascorbic acid solution was added to prevent oxidation, and the pH of the carrot pulp was set at 4.8 with a 10% citric acid solution. The pulp was divided in portions of 400 ml and to each portion 60 ml of water was added, with or without enzymes. The mixture was stirred in a 50° C. waterbath. Then 60 ml water or enzyme (2 500 endo-PG units) was added and the pulp was incubated for 3 hours while stirring slowly (20 to 30 rpm) at 50° C.

The endopolygalacturonase of the invention was compared with endo-polygalacturonase II of *Aspergillus tubigensis* (H. J. D. Bussink, H. C. M. Kester, J. Visser (1990) FEBS Lett 273, 127–130) and with the commercial enzyme Rohament P (Roehm), a classical *Aspergillus niger* preparation, containing a variety of lpectin-degrading enzymes. A reference trial was done without any added enzyme.

Figure 4:
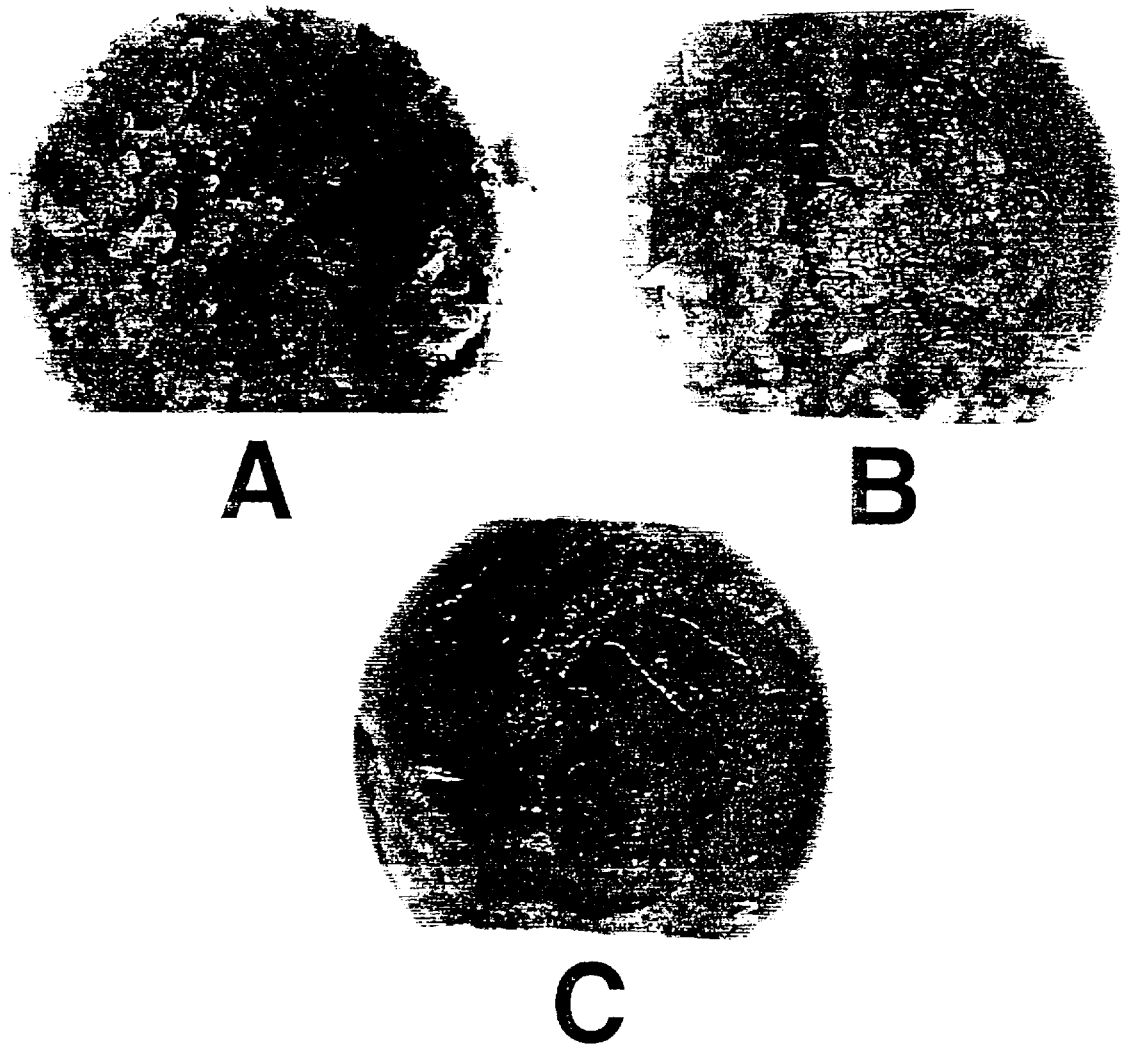
FIG. 4 (A–C) shows the effect of the enzyme of the invention in the production of puree.

FIG. 4A shows the result of the reference trial, FIG. 4B shows the result of the Rohament® P enzyme preparation, and FIG. 4C shows the result of the endopolygalacturonase of the invention. The result of endopolygalacturonase II was identical to the Rohament® P result.

In the reference trial there was no formation of puree. The pulp stayed at the stage of small pieces. Treatment with Rohament® P or endopolygalacturonase resulted in a puree that was smoother than the reference trial, but still contained small pieces. Treatment with the endopolygalacturonase of the invention resulted in the formation of a very smooth puree without any pieces.

This shows that the endopolygalacturonase of the invention is a very good maceration enzyme wich can be used for the production of carrot purees

What is claimed is:

1. A recombinant polynucleotide molecule which comprises an encoding nucleotide sequence that encodes a protein having endopolygalacturonase activity, said protein having an amino acid sequence at least 95% homologous to SEQ. ID. No.: 2.

2. The recombinant polynucleotide molecule of claim 1 wherein the encoding nucleotide sequence is operably linked to one or more expression regulatory sequences capable of directing expression therefrom in a host cell.

3. A vector comprising the polynucleotide molecule of claim 1 or 2.

4. A recombinant or isolated protein which has endopolygalacturonase activity, wherein said protein has an amino acid sequence at least 95% homologous to SEQ. ID. No.: 2.

5. A microbial host cell comprising the recombinant polynucleotide molecule of claim 1 or 2.

6. A method for preparing recombinant endopolygalacturonase, which method comprises culturing a microbial host cell according to claim 5 under conditions for expression of said encoding nucleotide sequence.

7. A food or feed composition or a detergent composition comprising the protein of claim 4.

8. The polynucleotide molecule of claim 1 or 2, wherein said encoding nucleotide sequence encodes a protein having the amino acid sequence of SEQ. ID. No.: 2.

9. A recombinant polynucleotide molecule which encodes a protein having endopolygalacturonase activity, wherein said encoding nucleotide sequence is at least 95% homologous to SEQ. ID. No.: 1.

10. The recombinant polynucleotide molecule of claim 9, wherein said encoding nucleotide sequence is SEQ. ID. No.: 1.

11. The protein of claim 4, which has the amino acid sequence of SEQ. ID. No.: 2.

12. A food or feed composition comprising the protein of claim 11.

13. A detergent composition comprising the protein of claim 11.

14. A recombinant or isolated protein having polygalacturonase activity that is encoded by the encoding nucleotide sequence of claim 9.

15. A recombinant or isolated protein having polygalacturonase activity that is encoded by the encoding nucleotide sequence of claim 10.

16. A food or feed composition comprising the protein of claim 14 or 15.

17. A detergent composition comprising the protein of claim 14 or 15.

* * * * *

SEQUENCE LISTING

```
<160> NUMBER OF SEQ ID NOS: 2

<210> SEQ ID NO 1
<211> LENGTH: 1570
<212> TYPE: DNA
<213> ORGANISM: Aspergillus tubingensis
<220> FEATURE:
<221> NAME/KEY: CDS
<222> LOCATION: (172)...(1260)

<400> SEQUENCE: 1
gcttgtgttt cttaggagaa ttattattct tttgttatgt tgcgcttgta gttggaaaag      60
gtgaagagac aaagcttgaa ttcctctttc ttctcttttcc tttcccagct tctctctagt    120
ccttccttaa ttgtacccgg ttgatccagg ttccattcct tcgttttcac c atg cac     177
                                                         Met His
                                                           1 ttc ctc cag aac gct ttc gtg gcc gcc act atg ggc gct gcg ctg gcc      225
Phe Leu Gln Asn Ala Phe Val Ala Ala Thr Met Gly Ala Ala Leu Ala
              5                  10                  15 gcc gct gct cct ctt gag aag cgc tcc tgc act ttc acc tcc gct tct      273
Ala Ala Ala Pro Leu Glu Lys Arg Ser Cys Thr Phe Thr Ser Ala Ser
         20                  25                  30 gct gcc aag tct ggc aag tcc tct tgc acc acc atc acc ctc gac aac      321
Ala Ala Lys Ser Gly Lys Ser Ser Cys Thr Thr Ile Thr Leu Asp Asn
 35                  40                  45                  50 atc gag gtc ccc gcc ggt gag act ctt gac ttg act ggc ctc aag aag      369
Ile Glu Val Pro Ala Gly Glu Thr Leu Asp Leu Thr Gly Leu Lys Lys
                 55                  60                  65 ggt act acc gtc atc ttc gag ggt gaa acc acc ttc ggc tac aag gaa      417
Gly Thr Thr Val Ile Phe Glu Gly Glu Thr Thr Phe Gly Tyr Lys Glu
             70                  75                  80
```

```
tgg aag ggt ccc ctg atc tcc atg tcc ggt acc gac atc acc gtc aag    465
Trp Lys Gly Pro Leu Ile Ser Met Ser Gly Thr Asp Ile Thr Val Lys
        85                  90                  95 cag gcc tcc ggt gcc aag atc aac tgc gac ggt gct cgc tgg tgg gac    513
Gln Ala Ser Gly Ala Lys Ile Asn Cys Asp Gly Ala Arg Trp Trp Asp
        100                 105                 110 ggc aag ggt agc aac ggt ggc aag acc aag ccc aag ttc ttc cag gtc    561
Gly Lys Gly Ser Asn Gly Gly Lys Thr Lys Pro Lys Phe Phe Gln Val
115                 120                 125                 130 cac aag ctc gac gag tcc agc atc acc ggc ctg aag atc tac aac acc    609
His Lys Leu Asp Glu Ser Ser Ile Thr Gly Leu Lys Ile Tyr Asn Thr
                135                 140                 145 cct gtc cag ggc ttc agc att ctg gct gac cac ctg acc atc act gac    657
Pro Val Gln Gly Phe Ser Ile Leu Ala Asp His Leu Thr Ile Thr Asp
        150                 155                 160 gtg acc att gac aac tcc gcc ggt acg agc aag ggc cac aac acc gat    705
Val Thr Ile Asp Asn Ser Ala Gly Thr Ser Lys Gly His Asn Thr Asp
        165                 170                 175 gcc ttt gac att ggt cag agt acc tac atc acc atc gac ggt gcc acc    753
Ala Phe Asp Ile Gly Gln Ser Thr Tyr Ile Thr Ile Asp Gly Ala Thr
        180                 185                 190 gtc tac aac cag gat gat tgc ctg gcc atc aac tcg ggt gag cac atc    801
Val Tyr Asn Gln Asp Asp Cys Leu Ala Ile Asn Ser Gly Glu His Ile
195                 200                 205                 210 act ttc acc aac ggt tac tgt gac ggt ggc cac ggt ctc tcc att ggt    849
Thr Phe Thr Asn Gly Tyr Cys Asp Gly Gly His Gly Leu Ser Ile Gly
                215                 220                 225 tcc att ggt ggc cgc agc gac aac acc gtc aac gac gtg acc atc tcc    897
Ser Ile Gly Gly Arg Ser Asp Asn Thr Val Asn Asp Val Thr Ile Ser
        230                 235                 240 aac tcc aag gtg ctc aac tcc cag aac ggt gtc cgt atc aag acc atc    945
Asn Ser Lys Val Leu Asn Ser Gln Asn Gly Val Arg Ile Lys Thr Ile
        245                 250                 255 tac ggc aag acc ggc act gtt gag aac gtc aag ttc gag gac atc acc    993
Tyr Gly Lys Thr Gly Thr Val Glu Asn Val Lys Phe Glu Asp Ile Thr
        260                 265                 270 ctg tcc gac atc agc aag tac ggt atc gtc gtt gag cag gac tac gag    1041
Leu Ser Asp Ile Ser Lys Tyr Gly Ile Val Val Glu Gln Asp Tyr Glu
275                 280                 285                 290 aac ggc agc ccc acc ggc acg ccc acc aac ggt gtc aag gtt gag gac    1089
Asn Gly Ser Pro Thr Gly Thr Pro Thr Asn Gly Val Lys Val Glu Asp
                295                 300                 305 atc act ttc aag aag gtc acc ggc agc gtc aag agc tct ggt act gac    1137
Ile Thr Phe Lys Lys Val Thr Gly Ser Val Lys Ser Ser Gly Thr Asp
        310                 315                 320 atc tac atc ctg tgc ggt tcc ggc agc tgc tcg aac tgg acc tgg agc    1185
Ile Tyr Ile Leu Cys Gly Ser Gly Ser Cys Ser Asn Trp Thr Trp Ser
        325                 330                 335 ggt gtt gat gtg acc ggc ggc aag aag agc agc aag tgc aag aac gtc    1233
Gly Val Asp Val Thr Gly Gly Lys Lys Ser Ser Lys Cys Lys Asn Val
340                 345                 350 ccc tcg ggc gct tct tgc agc gac taa gcggtctctt gatagctatg          1280
Pro Ser Gly Ala Ser Cys Ser Asp  *
355                 360 tcgaggtgtt gggccttaac tagtagtaag gctgcgtgag ggattttccg ttctggactc  1340
tggccgaatg ccggaagtgt ttgtattagc ttttaatgtt tagagtatca ttggaagaat  1400
agatgactcg agtctaatct aaaaaaaaaa aaaaaaaaa aaaactcgag aatttatact   1460
tagataagta tgtacttaca ggtatatttc tatgagatac tgatgtatac atgcatgata  1520
```

```
atatttaaac ggttattagt gccgattgtc ttgtgcgata atgacgttcc          1570
```

<210> SEQ ID NO 2
<211> LENGTH: 362
<212> TYPE: PRT
<213> ORGANISM: Aspergillus tubingensis

<400> SEQUENCE: 2

```
Met His Phe Leu Gln Asn Ala Phe Val Ala Ala Thr Met Gly Ala Ala
 1               5                  10                  15

Leu Ala Ala Ala Ala Pro Leu Glu Lys Arg Ser Cys Thr Phe Thr Ser
            20                  25                  30

Ala Ser Ala Ala Lys Ser Gly Lys Ser Ser Cys Thr Thr Ile Thr Leu
        35                  40                  45

Asp Asn Ile Glu Val Pro Ala Gly Glu Thr Leu Asp Leu Thr Gly Leu
    50                  55                  60

Lys Lys Gly Thr Thr Val Ile Phe Glu Gly Thr Thr Phe Gly Tyr
65                  70                  75                  80

Lys Glu Trp Lys Gly Pro Leu Ile Ser Met Ser Gly Thr Asp Ile Thr
                85                  90                  95

Val Lys Gln Ala Ser Gly Ala Lys Ile Asn Cys Asp Gly Ala Arg Trp
            100                 105                 110

Trp Asp Gly Lys Gly Ser Asn Gly Gly Lys Thr Lys Pro Lys Phe Phe
        115                 120                 125

Gln Val His Lys Leu Asp Glu Ser Ser Ile Thr Gly Leu Lys Ile Tyr
    130                 135                 140

Asn Thr Pro Val Gln Gly Phe Ser Ile Leu Ala Asp His Leu Thr Ile
145                 150                 155                 160

Thr Asp Val Thr Ile Asp Asn Ser Ala Gly Thr Ser Lys Gly His Asn
                165                 170                 175

Thr Asp Ala Phe Asp Ile Gly Gln Ser Thr Tyr Ile Thr Ile Asp Gly
            180                 185                 190

Ala Thr Val Tyr Asn Gln Asp Asp Cys Leu Ala Ile Asn Ser Gly Glu
        195                 200                 205

His Ile Thr Phe Thr Asn Gly Tyr Cys Asp Gly Gly His Gly Leu Ser
    210                 215                 220

Ile Gly Ser Ile Gly Gly Arg Ser Asp Asn Thr Val Asn Asp Val Thr
225                 230                 235                 240

Ile Ser Asn Ser Lys Val Leu Asn Ser Gln Asn Gly Val Arg Ile Lys
                245                 250                 255

Thr Ile Tyr Gly Lys Thr Gly Thr Val Glu Asn Val Lys Phe Glu Asp
            260                 265                 270

Ile Thr Leu Ser Asp Ile Ser Lys Tyr Gly Ile Val Val Glu Gln Asp
        275                 280                 285

Tyr Glu Asn Gly Ser Pro Thr Gly Thr Pro Thr Asn Gly Val Lys Val
    290                 295                 300

Glu Asp Ile Thr Phe Lys Lys Val Thr Gly Ser Val Lys Ser Ser Gly
305                 310                 315                 320

Thr Asp Ile Tyr Ile Leu Cys Gly Ser Gly Ser Cys Ser Asn Trp Thr
                325                 330                 335
```

-continued

```
Trp Ser Gly Val Asp Val Thr Gly Gly Lys Lys Ser Ser Lys Cys Lys
            340                 345                 350

Asn Val Pro Ser Gly Ala Ser Cys Ser Asp
            355                 360
```